(12) United States Patent
Wang et al.

(10) Patent No.: US 10,512,447 B2
(45) Date of Patent: Dec. 24, 2019

(54) PROBE HOLDING TABLE AND MEDICAL DEVICE

(71) Applicant: Edan Instruments, Inc., Shenzhen (CN)

(72) Inventors: Gonghua Wang, Shenzhen (CN); Kai Yang, Shenzhen (CN); Chuanxi Guo, Shenzhen (CN); Yong Wu, Shenzhen (CN)

(73) Assignee: Edan Instruments, Inc., Shenzhen, Guangdong Province (CN)

( * ) Notice: Subject to any disclaimer, the term of this patent is extended or adjusted under 35 U.S.C. 154(b) by 330 days.

(21) Appl. No.: 15/528,326

(22) PCT Filed: Dec. 19, 2016

(86) PCT No.: PCT/CN2016/110712
§ 371 (c)(1),
(2) Date: May 19, 2017

(87) PCT Pub. No.: WO2017/177712
PCT Pub. Date: Oct. 19, 2017

(65) Prior Publication Data
US 2018/0192992 A1    Jul. 12, 2018

(30) Foreign Application Priority Data

Apr. 15, 2016 (CN) .................... 2016 2 0317840 U
Apr. 15, 2016 (CN) .................... 2016 2 0318233 U

(51) Int. Cl.
*A61B 8/00* (2006.01)
*G01Q 70/02* (2010.01)

(52) U.S. Cl.
CPC .............. *A61B 8/42* (2013.01); *G01Q 70/02* (2013.01)

(58) Field of Classification Search
CPC ........................... H01R 39/00; Y10S 439/929
(Continued)

(56) References Cited

U.S. PATENT DOCUMENTS 3,652,972 A     3/1972  Kreider
3,794,952 A *   2/1974  Dowis .................... H01R 39/00
                                                              211/78
(Continued)

FOREIGN PATENT DOCUMENTS

CN         2647261 Y    10/2001
CN      201806784 U     4/2011
(Continued)

OTHER PUBLICATIONS

The EESR issued by EP Office dated Sep. 3, 2018.

*Primary Examiner* — Samuel G Gilbert
(74) *Attorney, Agent, or Firm* — Yunling Ren

(57) ABSTRACT

The disclosure provides a probe holding table and a medical equipment. The probe holding table comprises a faceplate and a fixing plate for supporting the faceplate. The faceplate is rotatably connected to the fixing plate. A plurality of probe placement units for installing probes are disposed on the faceplate, and each of the probe placement units is in electrical communication with an external power. The user may turn the faceplate to take the probes on the corresponding position, in particular, when more probes need to be used, the structure of the probe holding table is simpler than the normal fixed table, and easier to take the probes. Therefore, the medical equipment adopted the above probe holding table provides with the above advantages.

19 Claims, 10 Drawing Sheets

(58) Field of Classification Search
 USPC .......................................................... 128/897
 See application file for complete search history.

(56) References Cited

U.S. PATENT DOCUMENTS

| | | | |
|---|---|---|---|
| 4,016,511 A | 4/1977 | Ramsey et al. | |
| 5,178,546 A | 1/1993 | Dickerson | |
| 7,296,775 B2* | 11/2007 | Mayer | H01R 25/006 |
| | | | 211/163 |
| 9,054,476 B1* | 6/2015 | Reynolds | H01R 39/64 |
| 2011/0177703 A1* | 7/2011 | Lin | A47B 21/06 |
| | | | 439/131 |

FOREIGN PATENT DOCUMENTS

| | | |
|---|---|---|
| CN | 203122359 U | 8/2013 |
| CN | 103607530 A | 2/2014 |
| CN | 204034030 U | 12/2014 |
| CN | 204049874 U | 12/2014 |
| CN | 204494332 U | 7/2015 |
| CN | 204863260 U | 12/2015 |
| CN | 205598015 U | 9/2016 |
| CN | 205693117 U | 11/2016 |
| DE | 102005046465 A1 | 4/2007 |

* cited by examiner

PROBE HOLDING TABLE AND MEDICAL DEVICE

TECHNICAL FIELD

The present disclosure relates generally to medical instruments, and more specifically to a probe holding table and a medical equipment.

BACKGROUND

A fetal heart monitoring equipment often monitors several pregnant women at the same time, so the equipment must be equipped with a plurality of probes. Accordingly, it is important to place the probes at positions easily accessible for medical staff. At present, probes are disposed on a top or sides of a medical equipment. According to the traditional way of disposing probes, the probes can not be moved, and when there are many probes they would overlay each other, therefore, the medical staff still cannot easily to take the probes. It is not easy to change the number of the probes, if more probes are used, it would be difficult for a user to take and place the probes.

SUMMARY

In order to overcome the shortcomings mentioned above, the disclosure provides a probe holding table and a medical equipment of using the same. In the probe holding table, positions of the probes may be changed.

In order to solve the technical problems, the disclosure is as follows:

A probe holding table comprising: a faceplate; and a fixing plate supporting the faceplate. The faceplate is rotatably connected to the fixing plate, a plurality of probe placement units for installing probes are disposed on the faceplate, and each of the probe placement units is electrically connected to a external power.

Further, each of the probe placement units comprises a socket electrically connected to a corresponding probe and a probe slot receiving the probe.

Further, the probe holding table may comprise a first ring and a second ring. The first ring is rotatablely connected to the second ring, and one of the first ring and the second ring is fixedly connected to the faceplate, and the other one is fixedly connected to the fixing plate.

Further, the first ring may be sleeved on outside of the second ring, and the first ring and the second ring may be concentric rings.

Further, a first groove and a second groove are respectively disposed on adjacent sides of the first and second rings, and rolls are disposed between the first and second grooves.

Further, the faceplate may have a supporting plate disposed thereon. Moreover, the supporting plate may have a shape of ring, and the supporting plate may be disposed on a lower surface of the faceplate.

Further, the supporting plate may have a first locating pin disposed thereon, and the fixing plate may have a second locating pin disposed thereon. Moreover, a locating hole in one of the first and second rings may be correspondingly connected to the first locating pin, and a locating hole in the other one of the first and second rings may be correspondingly connected to the second locating pin.

Further, one of the first and second rings may be fastened to the supporting plate by screws, and the other one of the first and second rings may be fastened to the fixing plate by screws.

Further, a through hole may be formed in the middle of the faceplate, circular conductive rails are disposed on an inner sidewall of the through hole, the conductive components may be fixedly arranged on the fixing plate, and the conductive components may be electrically connected to the conductive rails, and the probe placement unit is electrically connected to the conductive rails.

Further, the conductive components are evenly disposed on the fixing plate.

Further, a fixing mount for fixing the conductive rails is disposed on the inner sidewall of the through hole, and the conductive rails are embedded in the fixing mount.

Further, the fixing mount is snapped to the conductive rails.

Further, lugs are disposed on a side of the fixing mount opposite to the conductive rails, and the lugs are electrically connected to the conductive rails.

Further, each of the conductive components may comprise a base and a conductive connector. Moreover, the base is fixed onto the fixing plate, and the conductive connector is connected to the base by a connecting rod, the connecting rod extends in a radial direction of the conductive rails, the conductive connector is conductive connected to the conductive rails, and an elastic member is sleeved on the connecting rod, and the elastic member is compressed between the conductive connector and the conductive rails.

Further, the base comprises a bottom portion fixedly connected to the fixing plate and a supporting portion fixedly connected to the bottom portion, a sleeve is disposed on the supporting portion, an opening end of the sleeve directs to the conductive rails, and an opposite end of the sleeve is closed, and the connecting rod and the elastic member are both received in the sleeve, and both ends of the elastic member respectively abut on the conductive connector and the closed end of the sleeve.

Further, a plurality of sleeves are disposed on the supporting portion of the base, and each of the sleeves is corresponding to mounting of one connecting rod, one elastic member, and one conductive connector, and each of the conductive connectors is electrically connected to a corresponding one of the conductive rails.

Further, each of the conductive components may comprise a spacing element, and an end of the connecting rod away from the conductive connector may pass through from the closed end of the sleeve to be snapped to the spacing element.

Further, the spacing element may be a retaining ring, and an end of the connecting rod away from the conductive connector may have a clamping slot. Moreover, the retaining ring may be snapped to the retaining ring.

Further, the conductive connector may comprise a conductive roller, a holder, and a shaft. Moreover, the conductive roller may be rotatably disposed on the holder by the shaft, the holder may be connected to the connecting rod, and the conductive roller may be in electrical communication with the conductive rails Further, an end of the connecting rod away the conductive connector has a terminal disposed thereon Further, a medical equipment is provided. The medical equipment comprises a probe holding table and a plurality of power consumption units.

Further, the probe holding table comprises: a faceplate; and a fixing plate supporting the faceplate is rotatably connected to the fixing plate. The faceplate is rotatably connected to the fixing plate, a plurality of probe placement units for installing probes are disposed on the faceplate, and each of the probe placement units is electrically connected to an external power.

Further, the power consumption units are circularly disposed on the faceplate, and each of the power consumption units is electrically connected to the probe holding table.

Compared with the related art, in the probe holding table of the disclosure, the faceplate may be rotatably connected to the fixing plate. That is, the probes are installed on the rotatably faceplate, and every probe placement unit may ensure electrical communication with the external power. Therefore, the medical staff can arbitrarily use any of the probes on the probe placement unit by rotating the faceplate to make the probe face to the patient, and avoid stacking of the probes. So it is easy for the medical staff to distinguish and pick up these probes. The medical staff can arbitrarily use any of the probes on the faceplate, operation is facilitated and working efficiency is increased accordingly.

The medical equipment of using the same also has advantages of the above.

REFERENCE NUMERAL LIST

10—probe holding table;
11—faceplate;
111—through hole;
112; supporting plate;
113: first locating pin;
115: fixing mount;
12: fixing plate;
121: second locating pin;
14: probe placement unit;
15: turntable;
151: first ring;
152: second ring;
153: first groove;
154: second groove;
155: spacing plate;
16: roll;
17: conductive rail;
18: conductive component;
181: base;
182: conductive connector;
1821: conductive roller;
1822: holder;
1823: shaft;
183: connecting rod;
184: elastic member;
185: bottom portion;
186: supporting portion;
187: sleeve;
188: spacing element;
20: power consumption unit;
21: probe;
30: frame; and
40: ire

DETAILED DESCRIPTION

Embodiments of the disclosure will now be described in detail. It may be understand that the disclosure may be varied in different embodiments without departing the scope of the disclosure. Hereinafter, the disclosure will be explained with reference to the accompanying drawings. The means of drawings is illustrate the essentially means of the disclosure, rather than to limit the disclosure.

Figure 1:
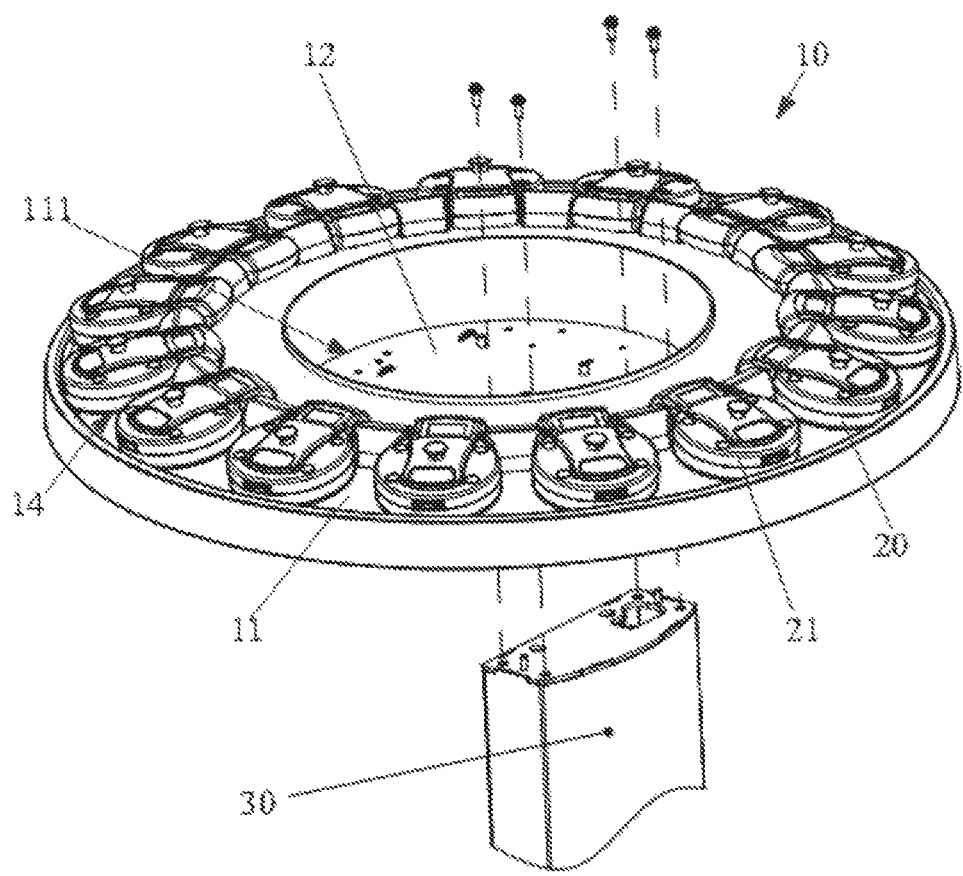
FIG. 1 is a perspective view showing the probe holding table of an embodiment of the disclosure.

The disclosure provides a medical equipment. The medical equipment comprises a probe holding table 10 and a plurality of power consumption units 20. The power consumption units 20 are circularly disposed on a faceplate, and each of the power consumption units 20 is electrically connected to the probe holding table. As shown in FIG. 1, a plurality of probes 21 may be disposed in the probe holding table 10 via a plurality of probe placement units. The probe placement units are used for installing the probes. It may be understood that the probe placement unit may be used for other parallel power consumption units 20. In this embodiment, the probe 21 is just an example, and others are omitted for sake of simplicity.

In the embodiment, the probe holding table 10 comprises a faceplate 11 and a fixing plate 12 for supporting the faceplate 11. The faceplate 11 is rotatably connected to the fixing plate 12. A plurality of probe placement units for installing probes 21 are disposed on the faceplate 11, and each of the probe placement units 14 is electrically connected to an external power.

The faceplate 11 may be rotatably connected to the fixing plate 12 in the probe holding table 10 of the disclosure. The probes are disposed on the rotatable faceplate. Every probe placement unit 14 may be electrically connected to the external power reliably. The medical staff can select any one of the probes 21 on the probe placement unit 14 according to their requirement, and align the probe 21 to the patient by rotating the faceplate 11, such as to avoid stacking of the plurality of probes 21. Therefore the medical staff may easily distinguish and move these probes. Since the medical staff can arbitrarily use any probe 21 on the faceplate 11, operation is facilitated and operation efficiency is increased.

The faceplate 11 comprises a circular structure with a through hole 111 formed in the middle thereof. A plurality of probe placement units 14 are disposed on the on a circular upper surface of the faceplate. The probe placement units 14 are evenly disposed on the circular surface of the faceplate 11, so as to arrange the probes 21 as more as possible and expand the capacity of the faceplate 11 for receiving the probes 21. In addition, the circular surface of the faceplate 11 is arched, that is, the probe placement units 14 are disposed on the arched and raised upper surface of the faceplate 11, so as to facilitate to take the probes 21.

Figure 4:
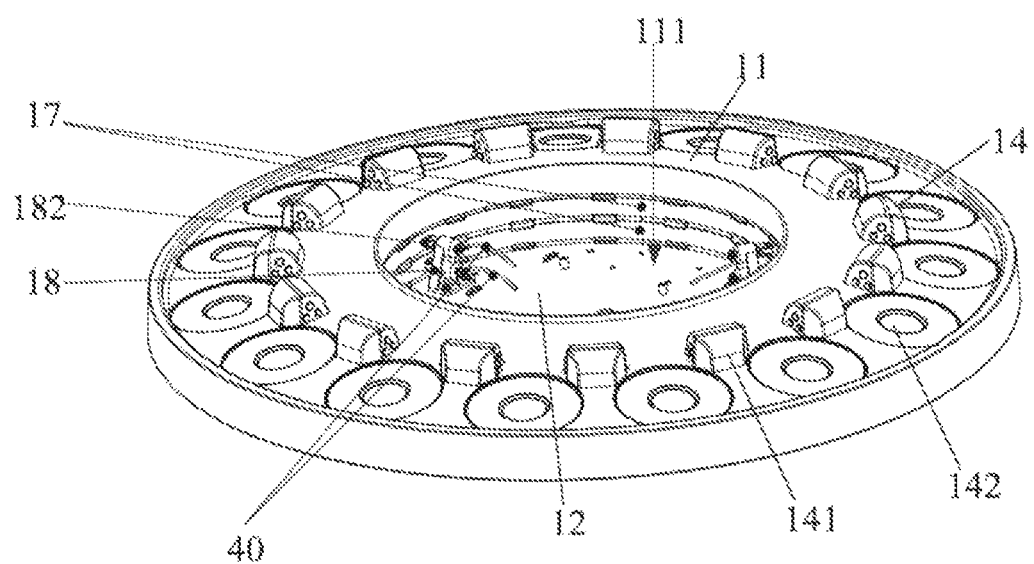
FIG. 4 is a perspective view showing the probe holding table of another embodiment of the disclosure.

As shown in FIG. 4, each of the probe placement units 14 comprises a socket 141 electrically connected to one of the probes 21 and a probe slot 142 receiving the probe 21. It may be understood that the probe 21 may include one or more rechargeable batteries, and the socket 141 may be a rechargeable fixed socket which may recharge the rechargeable battery. The socket 141 may have a elastic clip disposed thereon for fixing the probe 21. The probe slot 142 is used for retractably receiving the probe 21. When the probe 21 is used, the probe 21 is pulled out from the probe slot 142, and after used, the probe 21 may be automatically retracted back to the probe slot 142.

Figure 2:
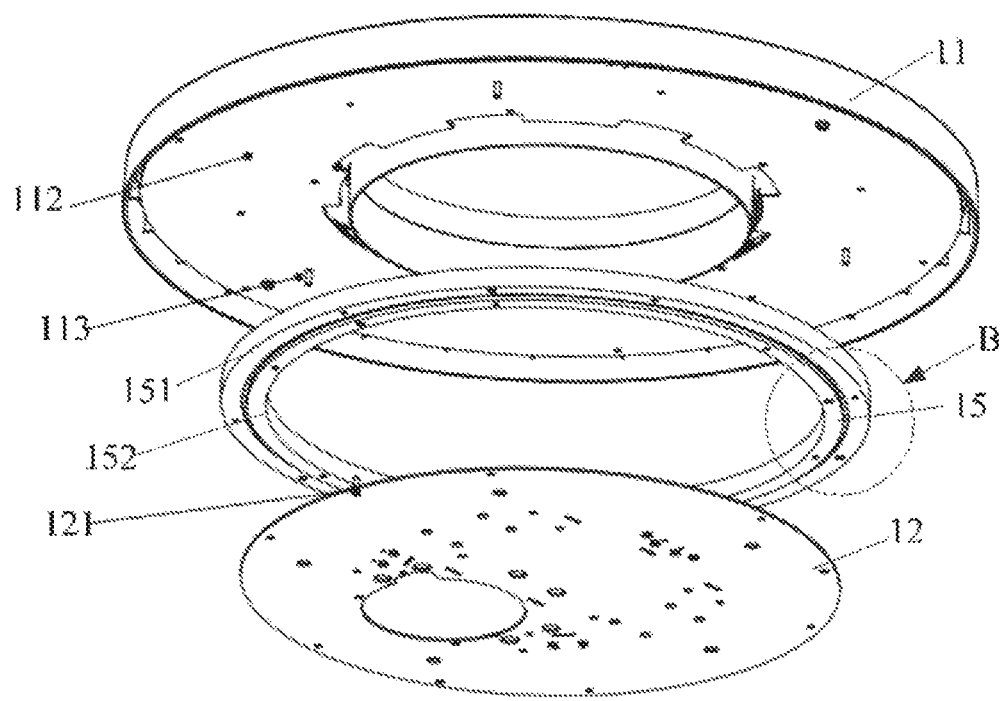
FIG. 2 is a bottom view showing the probe holding table of FIG. 1.

As shown in FIG. 2, in the embodiment, the bottom surface of the faceplate 11 has a supporting plate 112 is disposed thereon. The supporting plate 112 has a shape of ring. The shape of the supporting plate 112 is corresponding to the shape of the faceplate 11. The supporting plate 112 is used for enhancing the strength and the bearing capacity of the faceplate 11, such that the supporting plate 112 may deform under the pressure of an increased number of the probes 21.

The fixing plate 12 is a circular slab. The fixing plate 12 is provided with respect to the through hole 111 of the faceplate 11. The center region of the fixing plate 12 is provided with an assembly mounting region. The components comprise a main control board of an ultrasonic equipment, a management circuit board of the probe 21, and motherboard of a monitor and other equipments. When the fixing plate 12 is positioned on the work table for the medical staff, the faceplate 11 on which the plurality of probes are placed can be fixed, so as to facilitate the medical staff to take and place the probes 21.

Figure 3:
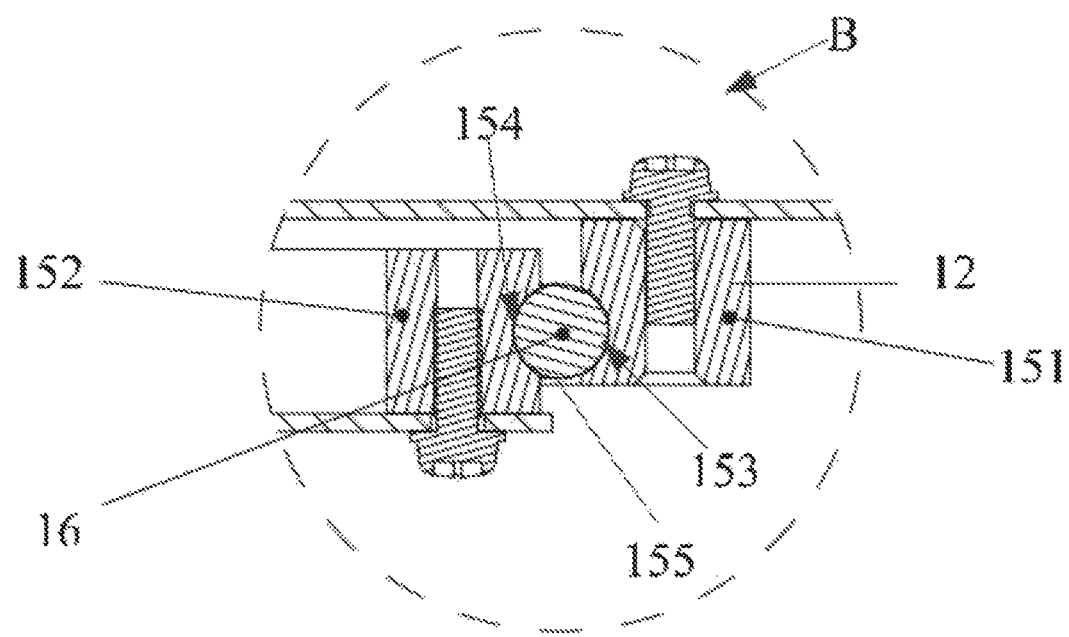
FIG. 3 is a cross section view showing a part B of the probe holding table of FIG. 2.

In the specific embodiment, the probe holding table 10 further comprises a turntable 15. The turntable 15 is positioned between the faceplate 11 and the fixing plate 12 and rotatably connects the faceplate 11 to the fixing plate 12. Specifically, as shown in FIG. 3, the turntable 15 comprises a first ring 151 and a second ring 152. A radius of the first ring 151 is larger than that of the second ring 152, and the first ring 151 is positioned on the outside of the second ring 152. The first ring 151 and the second ring 152 are concentric rings. The first ring 151 is rotatablely connected to the second ring 152. The first ring 151 and the second ring 152 may be rotated about a common center axis respectively without interfering with each other. So that the faceplate 11 and the fixing plate 12 may be rotated about the common center axis respectively without interfering with each other.

In the specific embodiment, the first ring 151 is fixedly connected to the faceplate 11, and the second ring 152 is fixedly connected to the fixing plate 12. Specifically, the first ring 151 is fixedly connected to the supporting plate 112 of the faceplate 11. The first ring 151 may be fastened to the supporting plate 112 via screws, and the second ring 152 may be fastened to the fixing plate 12 via screws. Moreover, the supporting plate 112 may have a first locating pin 113 disposed thereon, and the fixing plate 12 may have a second locating pin 121 disposed on. The first ring 151 and the second ring 152 each respectively defines a locating hole (not shown). The locating hole of the first ring 151 is correspondingly connected to the first locating pin 113, and the locating hole of the second ring 152 is correspondingly connected to the second locating pin 121, so as to perform positing of the supporting plate 112 and the fixing plate 12 with respect to each other when they are connected to different the rings on the turntable 15. There are pluralities of the first locating pins 113, the second locating pins 121, and, correspondingly, the positioning holes are evenly disposed, so as to ensure the first ring 151 is concentric with the faceplate 11, the second ring 152 is concentric with the fixing plate 12, thereby the turntable 15 may be steadily rotated with the faceplate 11 and the fixing plate 12 without displacement.

In other embodiments, the first ring 151 may be fixedly connected to the fixing plate 12, and the second ring 152 may be fixedly connected to the supporting plate 112 of the faceplate 11. As long as the first ring 151 and the second ring 152 are fixedly connected to the fixing plate 12 and the faceing plate 11, respectively, and the first ring 151 and the second ring 152 may be rotated with respect to each other, the fixing plate 12 and the faceplate 11 may be rotated with respect to each other.

As shown in FIG. 3, a first groove 153 and a second groove 154 are disposed on adjacent sides of the first ring 151 and the second ring 152, respectively. Rolls 16 are disposed between the first groove 153 and the second groove 154. That is, the first groove 153 is defined in an internal sidewall of the first ring 151, and the second groove 154 is defined in an outside sidewall of the second ring 152. The first groove 153 and the second groove 154 each has a cross section of a semi-circular groove. Moreover, the first groove 153 and the second groove 154 are disposed opposite to each other, so as to form a channel having a cross section of round. The rolls 16, being disposed between the first groove 153 and the second groove 154, may roll along the channel. When the first ring 151 and the second ring 152 are rotated with respect to each other, the rolls 16 may roll in the channel to reduce a frictional force between the first ring 151 and the second ring 152.

In one embodiment, the first groove 153 is located at a lower position in a middle portion of the internal sidewall of the first ring 151, and the second groove 154 is located at a middle position of the outside sidewall of the second ring 152. When the first ring 151 is sleeved on the outside of the second ring 152 and the first and second grooves are opposite to each other, the first ring 151 and the second ring 152 may be partially displaced up and down, such that the first ring 151, being slightly higher than the second ring 152, may be conveniently connected to the faceplate 11, and the second ring 152 which is slightly lower may be conveniently connected to the fixing plate 12. A spacing plate 155 pointing to the second ring 152 may be disposed in the bottom of the first ring 151. The spacing plate 155 may avoid the rolls 16 from rolling out. The rolls 16 may be balls.

In other embodiments, the first ring 151 and the second ring 152 may be stacked with a same axial. The ring located on the upper is fixedly connected to the faceplate 11, and the ring located on the down is fixedly connected to the fixing plate 12. In addition, in the stacked structure, grooves may be formed in the opposide sides of the first ring 151 and f the second ring 152, and the rolls may roll along the grooves. In this way, it is also possible to make the faceplate 11 and the fixing plate 12 rotate with respect to each other without interfering with each other.

Figure 5:
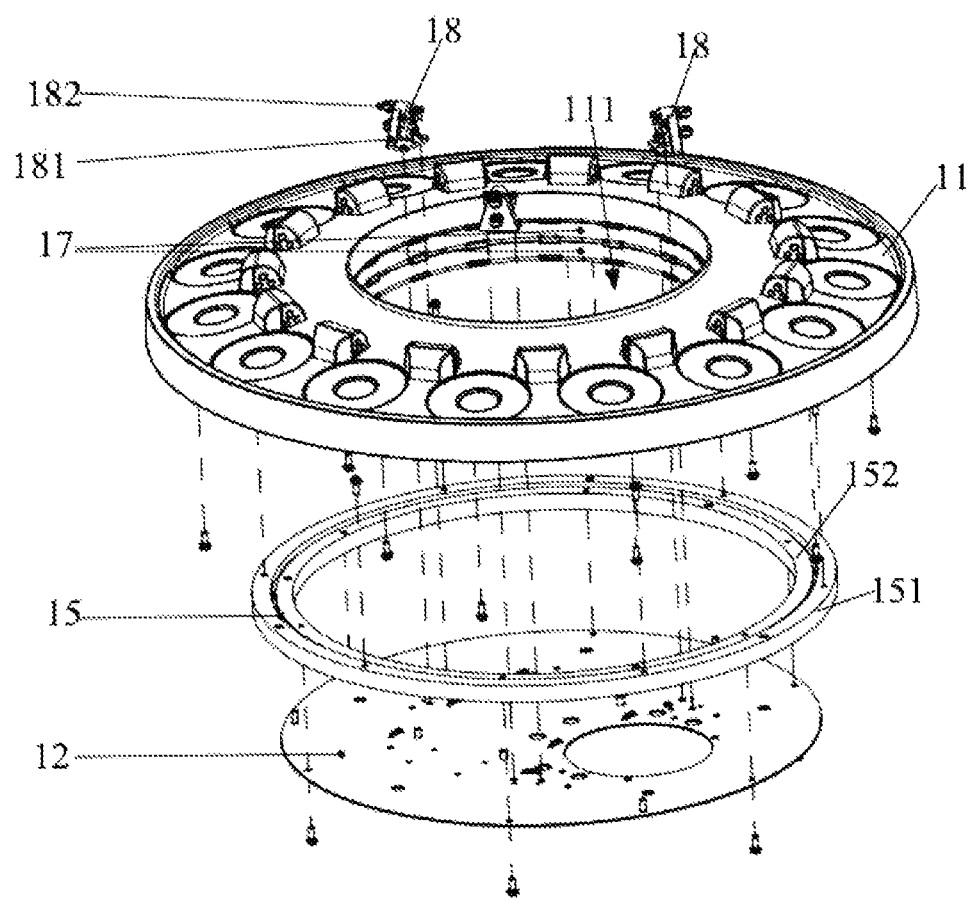
FIG. 5 is a perspective exploded view showing the probe holding table of FIG. 4.

As shown in FIGS. 4 and 5, circular electric conductive rails 17 are disposed on the inner sidewall of the through hole 111 of the faceplate 11. Conductive components 18 are fixedly arranged on the fixing plate 12. The fixing plate 12 may be fastened to the bottoms of the conductive components 18 via screw, clamping, or welding.

The conductive components 18 may be electrically connected to an external power. The conductive components 18 may be electrically connected to the conductive rails 17 which are electrically connected to the probe placement unit 14, so the probe placement unit 14 may be electrically connected to the external power. Moreover, the plurality of the conductive components 18 may be evenly disposed on the fixing plate 12. That is, the conductive components 18 are evenly disposed with respect to the conductive rails 17. The conductive components 18 may keep the electrical connection between the conductive components 18 and the conductive rails 17, so as to avoid break of the whole circuit due to a single damaged conductive component 18.

Figure 6:
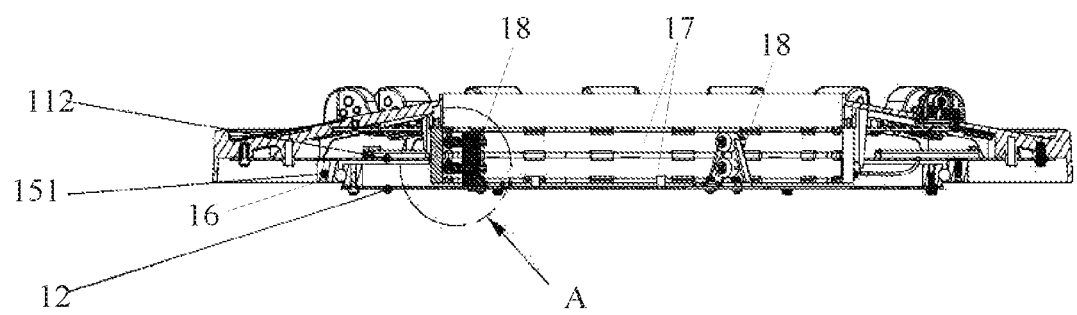
FIG. 6. is a sectional view showing the probe holding table of FIG. 4.
Figure 7:
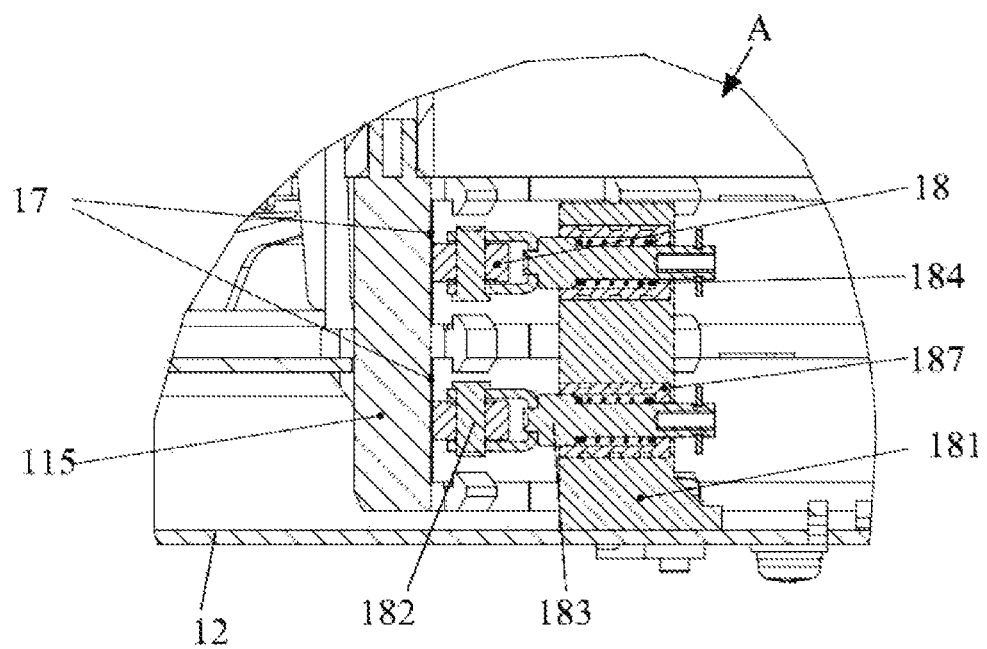
FIG. 7 is a partial magnification view showing a part A of the probe holding table of FIG. 4.

As shown in FIGS. 6 and 7, a fixing mount 115 for fixing the conductive rails 17 is disposed on the inner sidewall of the through hole 111, and the conductive rails 17 are embedded in the fixing mount 115. The conductive rails 17 may be embedded in the fixing mount 115 by assembling and injection molding. In the specific embodiment, some clamps or climps for fixing the conductive rails 17 may be disposed on the inner sidewall of the fixing mount 115, such that the fixing mount 115 may be snapped to the conductive rails 17 by clamping or climping.

In the specific embodiment, each conductive component 18 comprises a base 181 fixed onto the fixing plate 12 and an electric conductive connector 182. The conductive connector 182 is connected to the base 181 by a connecting rod 183, and the conductive connector 182 is electrically connected to one of the conductive rails 17. An elastic member 184 is sleeved on the connecting rod 183. The conductive connector 182 may have a relative elastic displacement in a radial direction of the conductive rails 17 by the elastic member 184 and the base 181. The extension direction of the elastic member 184 directs to the corresponding conductive rail 17. The conductive connector 182 may have a relative elastic displacement in a radial direction of the corresponding conductive rail 17 by the elastic member 184 and the base 181. The conductive connector 182 may be reliably connected to the inner sidewall of the conductive rail 17 under the elastic force of the elastic member 184, so as to achieve reliable conductivity.

Figure 8:
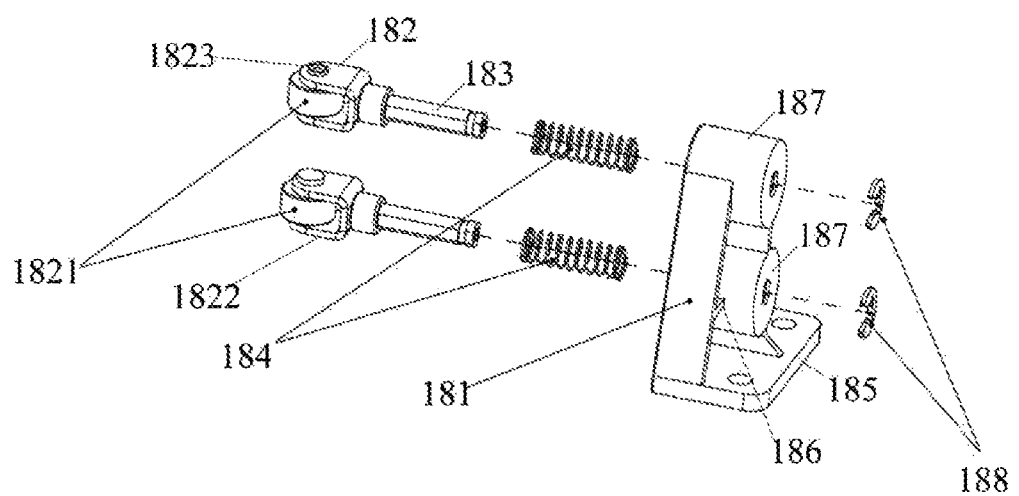
FIG. 8 is a perspective exploded view showing a conductive component of the probe holding table of FIG. 4.

As shown in FIG. 8, in the specific embodiment, each conductive component 18 comprises a base 181 and a conductive connector 182. The base 181 is fixed to the fixing plate 12. The base 181 comprises a bottom portion 185 fixedly connected to the fixing plate 12 and a supporting portion 186 fixedly connected to the bottom portion 185. A sleeve 187 is sleeved on the supporting portion 186. An opening end of the sleeve 187 directs to the conductive rails 17, and the opposite end is closed (closed end).

The conductive connector 182 is connected to the base 181 by the connecting rod 183 extending in the radial direction of the corresponding conductive rail 17. The conductive connector 182 is electrically connected to the conductive rail 17. Each of the conductive component 18 further comprises a spacing element 188. An end of the connecting rod 183 away the conductive connector 182 passes the sleeve 187 and is snapped to the spacing element. Specifically, the spacing element 188 may be a retaining ring, and an end of the connecting rod 183 away from the conductive connector 182 has a clamping slot. The retaining ring may snapped onto the clamping slot.

The elastic member 184 is sleeved on the connecting rod 183, and the connecting rod 183 and the elastic member 184 are both received in the sleeve 187. The ends of the elastic member 184 respectively abut on the conductive connector and the closed end of the sleeve 187. It may be appreciated, the elastic member 184 may be a spring, a spring washer or other resilient material having extensibility.

In each conductive component 18, the elastic member 184 is provided to abut on the corresponding conductive connector 182 and the base 181, such that the conductive connector 182 is prevented from being in rigid contact with the conductive connector 182, which may results in an unadjustable pressure on the conductive rails 17. When the direction of extension of the elastic member 184 is directed to the conductive rails 17, the elastic force of the elastic member 184 may cause the conductive connector 182 to stably contact with the conductive rails 17 and there is still a certain space for displacement/deformation. When the faceplate 11 drives the conductive rails 17 to rotate, it is difficult to ensure that the movement path of the conductive rails 17 is a perfect circular shape, however, a deformation resulted from this may be offseted by the contraction of the elastic member 184 abutting on the conductive connector 182, so that the relation rotation of the faceplate 11 and the fixing plate 12 is smooth and the power supply between each other is stable.

Figure 9:
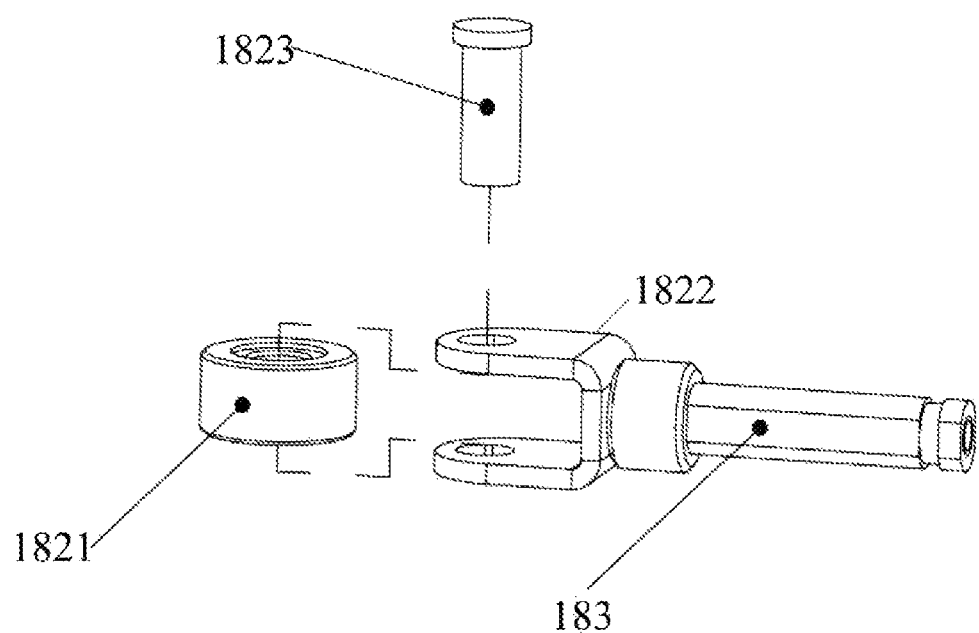
FIG. 9 is a perspective exploded view showing the conductive connector of the conductive component of FIG. 8.

As shown in FIG. 9, in the specific embodiment, each conductive connector 182 comprises an electric conductive roller 1821, a holder 1822 and a shaft 1823. The conductive roller 1821 is rotatably disposed on the holder 1822 by the shaft 1823. The holder 1822 is connected to a corresponding connecting rod 183. The conductive roller 1821 is in electric communication with the conductive rails 17. The faceplate 11 may drive the conductive rails 17 to rotate, and rotating of the conductive rails 17 may drive the conductive roller 1821 to roll. Since the friction between the conductive rails 17 and the conductive roller 1821 is rolling friction, wearing of the parts is significantly reduced, thereby the reliability of the product is enhanced.

In the specific embodiment, a plurality of sleeves 187 are disposed on the supporting portion of base 181. Each sleeve 187 is corresponding to mounting of one connecting rod 183, one elastic member 184, and one conductive connector 182. Moreover, a plurality of conductive rails 17 are provided, and each of the conductive connectors 182 is electrically connected to one corresponding conductive rail 17. At least two conductive rails 17 are provided. Each of the conductive components 18 is provided with a corresponding number of the conductive connectors 182 connected the conductive rails 17. Meanwhile, a plurality of sets of power supply components may be provided to cooperate with the conductive rails 17 at different angles, so that two or even more power supply circuits can be formed between the faceplate 11 and the fixing plate 12 to meet the requirement of power if a different number of probes 21 are provided on the faceplate 11.

In other embodiments, it would be understood that the conductive connector 182 of the conductive component 18 may be an electric brush passing the base 181. The elastic member 184 is placed between and abut on the electric brush and the base 181. The elastic force of the elastic member 184 may force the electric brush and the conductive rails 17 to elastically displace with respect to each other in the radial direction of the conductive rails 17 when the electric brush is slidably connected to the conductive rails 17. The structure of the electric brush may include, but is not limited to, a filament, a plate and so on.

Figure 10:
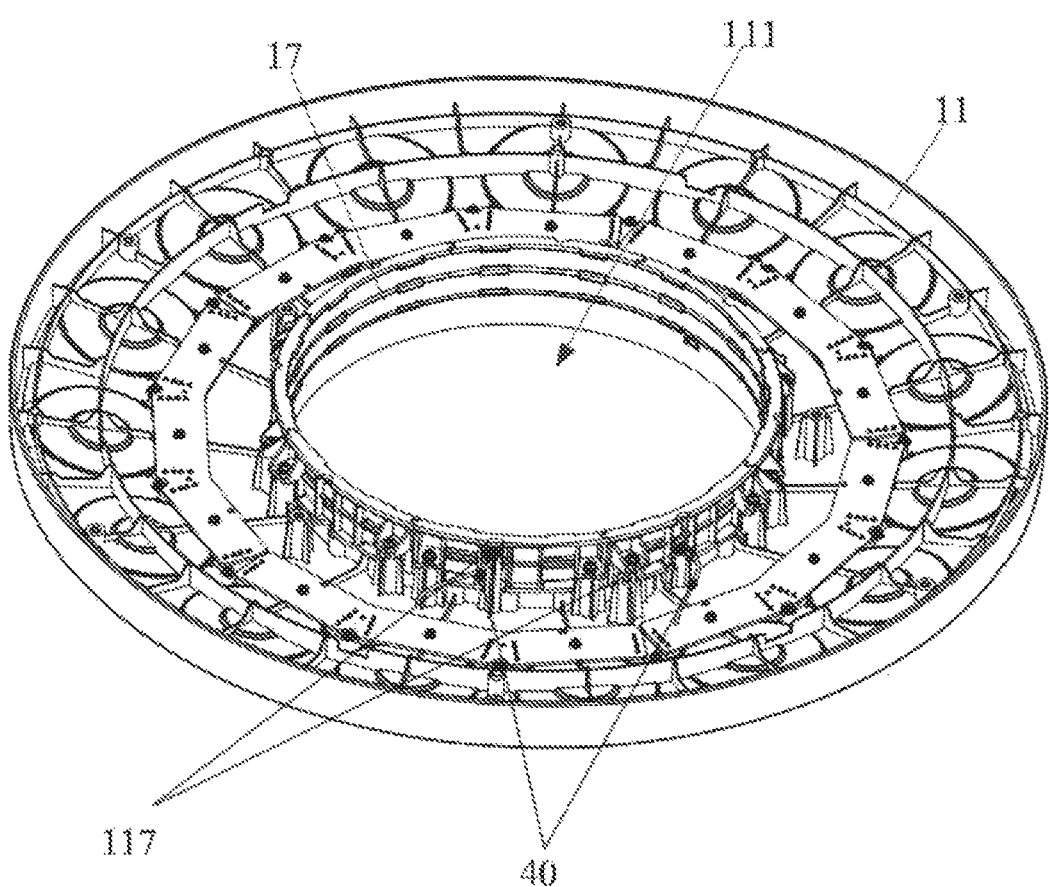
FIG. 10 is a bottom view showing the probe holding table of FIG. 4.

As shown in FIG. 10, the end of each connecting rod 183 away the conductive connector has a terminal disposed thereon (no shown). Lugs 117 are disposed on the side of the fixing mount 115 opposite to the conductive rails. The lugs 117 are electrically connected to the conductive rails 17. The terminals and the lugs 117 may facilitate electrical connecting of the wires 40 and the connecting rods 183 to the conductive rails 17, thus facilitating wiring of the medical equipment.

As shown in FIG. 10, the medical equipment provided in the disclosure further comprises a frame 30. The probe holding table 10 may placed on the frame 30, so as to facilitate movement of the probe holding table 10.

The embodiments described above are merely some preferable ones, and the disclosure is not limited to any specific details of these embodiments. An oridinary person skilled in the art would readily appreciate that modifications or changes based on the principles of the disclosure. Accordingly, the scope of the disclosure should be limited solely by the appended claims.

What is claimed is:

1. A probe holding table, comprising:
a faceplate; and
a fixing plate for supporting the faceplate; and
a first ring and a second ring,
wherein the first ring is rotatably connected to the second ring,
wherein one of the first ring and the second ring is fixedly connected to the faceplate, and the other is fixedly connected to the fixing plate,
wherein the faceplate is rotatably connected to the fixing plate, a plurality of probe placement units for installing probes are disposed on the faceplate, and each of the probe placement units is in electrical communication with an external power, and
wherein the first ring is sleeved outside of the second ring, and the first ring and the second ring are concentric rings.

2. The probe holding table according to claim 1, wherein each of the probe placement units comprises: a socket electrically connected to a corresponding probe, and a probe slot receiving the probe.

3. The probe holding table according to claim 1, wherein a first groove and a second groove are respectively disposed on adjacent sides of the first ring and the second ring, and rolls are disposed between the first groove and the second groove.

4. The probe holding table according to claim 1, wherein a supporting plate is disposed on the faceplate and has a shape of ring and is disposed on a lower surface of the faceplate.

5. The probe holding table according to claim 4, wherein a first locating pin is disposed on the supporting plate and a second locating pin is disposed on the fixing plate, and wherein a locating hole in one of the first and second rings is connected to the first locating pin, and a locating hole in the other of the first and second rings is connected to the second locating pin.

6. The probe holding table according to claim 4, wherein one of the first and second rings is fastened to the supporting plate by screws, and the other of the first and second rings is fastened to the fixing plate by screws.

7. The probe holding table according to claim 1, wherein a through hole is formed in the middle of the faceplate, a circular conductive rail is disposed on an inner sidewall of the through hole,
wherein a conductive component is fixedly arranged on the fixing plate, and wherein the conductive component is electrically connected to the conductive rail, and the probe placement unit is electrically connected to the conductive rail.

8. The probe holding table according to claim 7, wherein the conductive component is disposed in a plurality and evenly disposed on the fixing plate.

9. The probe holding table according to claim 7, wherein a fixing mount for fixing the conductive rail is disposed on the inner sidewall of the through hole, and the conductive rail is embedded in the fixing mount.

10. The probe holding table according to claim 9, wherein the fixing mount is snapped to the conductive rail.

11. The probe holding table according to claim 9, wherein lugs are disposed on a side of the fixing mount opposite to the conductive rail and electrically connected to the conductive rail.

12. The probe holding table according to claim 7, wherein the conductive component comprises a base and a conductive connector,
wherein the base is fixed onto the fixing plate, and the conductive connector is connected to the base by a connecting rod,
wherein the connecting rod extends in a radial direction of the conductive rail, and the conductive connector is conductively connected to the conductive rail, and
wherein an elastic member is sleeved on the connecting rod, and is compressed between the conductive connector and the conductive rail.

13. The probe holding table according to claim 12, wherein the base comprises: a bottom portion fixedly connected to the fixing plate; and a supporting portion fixedly connected to the bottom portion,
wherein a sleeve is disposed on the supporting portion, an opening end of the sleeve directs to the conductive rails, and an opposite end of the sleeve is closed, and
wherein the connecting rod and the elastic member are both received in the sleeve, and both ends of the elastic member respectively abut on the conductive connector and the closed end of the sleeve.

14. The probe holding table according to claim 13, wherein a plurality of sleeves are disposed on the supporting portion of the base, and each of the sleeves is corresponding to mounting of one connecting rod, one elastic member, and one conductive connector, and
wherein each of the conductive connectors is electrically connected to one corresponding conductive rail.

15. The probe holding table according to claim 12, wherein the conductive component further comprises a spacing element, and an end of the connecting rod away from the conductive connector passes through the closed end of the sleeve and is snapped to the spacing element.

16. The probe holding table according to claim 15, wherein the spacing element is a retaining ring, and
wherein an end of the connecting rod away from the conductive connector has a clamping slot, and the retaining ring is snapped to the clamping slot.

17. The probe holding table according to claim 12, wherein the conductive connector comprises a conductive roller, a holder, and a shaft, and
wherein the conductive roller is rotatably disposed on the holder by the shaft, the holder is connected to the connecting rod, and the conductive roller is in electrical communication with the conductive rail.

18. The probe holding table according to claim 12, wherein an end of the connecting rod away the conductive connector has a terminal disposed thereon.

19. A medical equipment, comprising:
the probe holding table according to claim 1, and
a plurality of power consumption units, circularly disposed on the faceplate, and each of the power consumption units is electrically connected to the probe holding table.

* * * * *